United States Patent
Stamler et al.

(10) Patent No.: US 7,956,062 B2
(45) Date of Patent: Jun. 7, 2011

(54) REACTIVE OXYGEN GENERATING ENZYME INHIBITOR WITH NITRIC OXIDE BIOACTIVITY AND USES THEREOF

(75) Inventors: Jonathan S. Stamler, Chapel Hill, NC (US); Eric J. Toone, Durham, NC (US); Joshua M. Hare, Baltimore, MD (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 12/554,249

(22) Filed: Sep. 4, 2009

(65) Prior Publication Data

US 2010/0010019 A1 Jan. 14, 2010

Related U.S. Application Data

(60) Division of application No. 11/430,986, filed on May 10, 2006, now Pat. No. 7,625,907, which is a continuation of application No. 10/829,940, filed on Apr. 23, 2004, now Pat. No. 7,067,659.

(51) Int. Cl.
*A61K 31/519* (2006.01)
*C07D 487/04* (2006.01)

(52) U.S. Cl. ..................... 514/262.1; 544/262

(58) Field of Classification Search ............... 514/262.1
See application file for complete search history.

(56) References Cited

U.S. PATENT DOCUMENTS

| 6,359,182 B1 | 3/2002 | Stamler et al. ............. 568/949 |
| 6,538,116 B2 | 3/2003 | Stamler et al. ............. 534/568 |
| 6,887,994 B2 | 5/2005 | Stamler et al. ............. 540/467 |
| 7,067,659 B2 | 6/2006 | Stamler et al. ............. 544/258 |
| 2003/0171393 A1 | 9/2003 | Soldato ................... 514/291 |
| 2003/0176668 A1 | 9/2003 | Stamler et al. ............. 534/566 |
| 2004/0006059 A1 | 1/2004 | Stamler et al. ............. 514/211.01 |
| 2006/0194820 A1 | 8/2006 | Stamler ................... 514/262.1 |

FOREIGN PATENT DOCUMENTS

EP 1336602 8/2003

OTHER PUBLICATIONS

No Author, "Trilateral Project B3b theme: Comparative study on reach-through claims" [online]. San Francisco, California, Nov. 5-9, 2001, [retrieved on Jun. 26, 2003]. Retrieved from the Internet <http://www.uspto.gov/web/tws/B3b_reachthrough.pdf>.
Beers, M. H., M.D., Editor-In-Chief, the Merck Manual $2^{nd}$ Home Edition, Chapters 25 and 33, 2005.
Sacks, H., et al., Am. J. Med., Feb. 1982, 72(2):233-40, Medline Abstract PMID: 7058834.
Norris, S. L., et al., (2005), Ann. Intern. Med., 142: 1112-1119 (Abstract).
Koppel, I. A., et al., J. Am. Chem. Soc., 124(19), 5594-5600 (English) 2002.
Fuchigami, T., et al., Denki Kagaku oyobi Kogyo Butsuri Kagaku, 44(12), 803-8 (Japanese) 1976, Abstract 86:97892 only.
No Author, PDR® entry for Nitrolingual® Pump Spray [online]Tthomson. Micromedex 2002-2005 [retrieved Jun. 27, 2006]. Retrieved from Internet <http://www.thomsonhc.com/pdrel/librarian/ND_PR/Pdr/PFPUI/q34KP3RPfNuqK/DDAK/DocumentAppData32025/ND_PG/DocB.
Center for Disease Control Prevention, Chronic Fatigue Syndrome, downloaded Jun. 26, 2009, <http://www.cdc.gov/cfs/cfstreatment.htm>, pp. 1-8.

*Primary Examiner* — Susanna Moore
(74) *Attorney, Agent, or Firm* — Bacon & Thomas, PLLC

(57) ABSTRACT

A reactive oxygen generating enzyme inhibitor with NO donor bioactivity, e.g., nitrated allopurinol, is useful to treat heart failure, stable angina, ischemic disorder, ischemic reperfusion injury, atherosclerosis, sickle cell disease, diabetes, Alzheimer's disease, Parkinson's disease, ALS and asthma and to obtain proper contraction of heart, skeletal and smooth muscle.

1 Claim, 1 Drawing Sheet

US 7,956,062 B2

REACTIVE OXYGEN GENERATING ENZYME INHIBITOR WITH NITRIC OXIDE BIOACTIVITY AND USES THEREOF

CROSS REFERENCE TO RELATED APPLICATIONS

This is a division of U.S. application Ser. No. 11/430,986, filed May 10, 2006, now U.S. Pat. No. 7,625,907, issued Dec. 1, 2009, which is a continuation of U.S. application Ser. No. 10/829,940, filed Apr. 23, 2004, now U.S. Pat. No. 7,067,659, issued Jun. 27, 2006.

TECHNICAL FIELD

This invention is directed to agent and method for treatment of disorders characterized by increased production of reactive oxygen species and insufficient production of nitric oxide.

BACKGROUND OF THE INVENTION

Current treatments of heart failure could use improvement.

An imbalance between left ventricle performance and myocardial oxygen coupling, which has been denoted mechanoenergetic uncoupling has been recognized as leading to cardiac insufficiency; conventional drugs for treatment of heart failure do not reverse this phenomenon. It has been shown that allopurinol and its metabolite oxypurinol may reverse this phenomenon.

It has not been previously appreciated that in disorders associated with oxidative stress, whereas allopurinol or oxypurinol may eliminate or reduce reactive oxygen species, they and compounds like them do not reduce an independent nitric oxide depletion effect, which, moreover, may be more than additive.

SUMMARY OF THE INVENTION

It has been discovered herein that in disorders associated with oxidative stress, there is an independent nitric oxide depletion effect.

One embodiment of the invention herein, denoted the first embodiment, is directed to an inhibitor of a reactive oxygen generating enzyme which includes a group providing nitric oxide (NO) donor bioactivity which is not a C-nitroso compound or an inhibitor of a cyclooxygenase.

Another embodiment of the invention herein, denoted the second embodiment, is directed to a method for treating a patient with a disorder associated with oxidative stress, comprising administering to that patient a therapeutically effective amount of the inhibitor of the first embodiment.

Another embodiment of the invention herein, denoted the third embodiment, is directed to a method for treating an ischemic disorder in a patient having such disorder, comprising administering to that patient an amount of the inhibitor of the first embodiment herein effective to mediate conservation of oxygen and vasodilation.

Another embodiment of the invention herein, denoted the fourth embodiment, is directed to a method for providing appropriate oxygen utilization in a patient in need thereof, comprising administering to that patient a therapeutically effective amount of the inhibitor of the first embodiment.

As used herein, the term "reactive oxygen" includes superoxide, hydroperoxide, other peroxides, peroxynitrite, alkoxides, hydroxyl radical and reactive nitrogen species.

As used herein, the term "providing NO donor bioactivity" means generating activity associated with NO or a related congener, e.g., dilation of a blood vessel or increased cGMP.

The term "appropriate oxygen utilization" as used in the description of the fourth embodiment means so as not to cause pathological increase in energy or oxygen use and/or pathological increase in radical or active oxygen species formation.

DETAILED DESCRIPTION

Figure 1A:
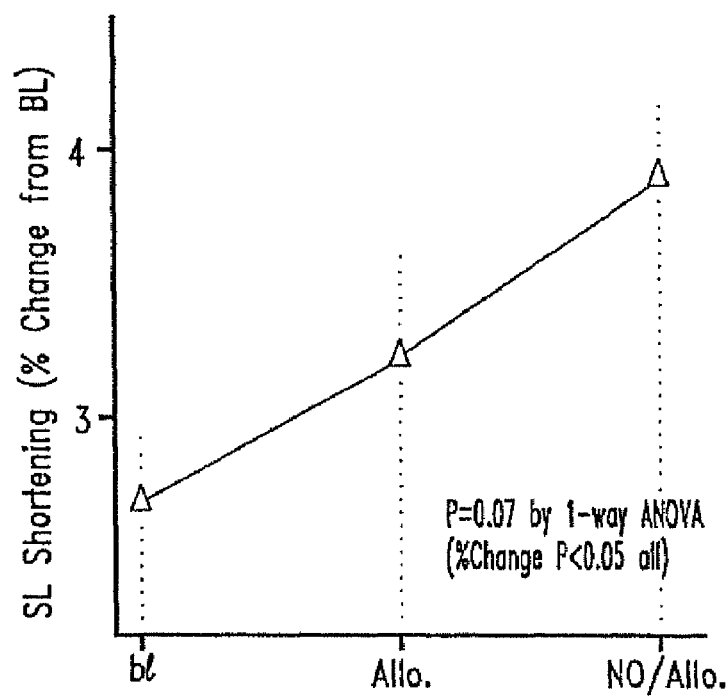
FIG. 1(a) is a graph of sacomere length (% change from baseline) for baseline, allopurinol administration and nitrated allopurinol administration and depicts results of Background Example 1.

We turn now to the first embodiment of the invention herein, which is directed to an inhibitor of a reactive oxygen generating enzyme which includes a group providing NO donor bioactivity which is not a C-nitroso compound or an inhibitor of a cyclooxygenase. The term "reactive oxygen generating enzyme" as used herein, excludes nitric oxide synthase.

The reactive oxygen generating enzymes include, for example, xanthine oxidase, epoxygenase, NADPH oxidase, aidehyde dehydrogenase, aldehyde oxidase, lipoxygenase, cytochrome p450 reductase, heme oxygenase, other oxygenases and oxidases and complex 1 and complex 3.

Inhibitors of xanthine oxidase include, for example allopurinol, oxypurinol, pterin-6-aldehyde and 6-formylpterin.

Inhibitors of epoxygenase include, for example, nordihydroguaiaretic acid, 17-octadecynoic acid, miconazole and ketoconazole.

Inhibitors of NADPH oxidase include, for example, diphenyl iodonium chloride or sulfate and apocynin.

Inhibitors of aldehyde dehydrogenase include, for example, bentomyl, disulfiram, phenethyl isothiocyanate and cyanamide.

Inhibitors of aldehyde oxidase include, for example, cimetidine, menadione and isovanillin.

Inhibitors of lipoxygenase include, for example, CV6504, ABT761, zileuton, linoleyl hydroxamic acid and panaxynol.

Inhibitors of cytochrome P450 reductase include mersalyl and diphenylene iodonium.

Inhibitors of heme oxygenase include, for example, pegylated zinc protoporphyrin, Co (III) protoporphyrin, Sn protoporphyrin and tin mesoporphyrin.

Inhibitors of complex 1 include, for example, retenone and MPTP.

Inhibitors of complex 3 include, for example, antinycin and 11-QoI MET.

The above inhibitors are furnished with NO donor bioactivity group, for example, by providing a nitrate group thereon, e.g., by forming a nitrate esters, or by providing a nitroso group thereon. The nitro or nitroso group is added to an area of the inhibitor that does not diminish binding to the target beyond an effective amount. One simple method of introducing this moiety is alkylation of any acidic site on the inhibitor by deprotonation and treatment with an alkyl halide. For example, a moiety containing a nitrate ester group can be substituted at the imido group of an inhibitor of a reactive oxygen generating enzyme by reacting 1-chloro-3-iodopropane in the presence of cesium carbonate. The resulting chloropropyl moiety is converted sequentially to an iodopropyl moiety and a nitrooxypropyl moiety by treatment with sodium iodide followed by silver nitrate in anhydrous $CH_3CN$. Other donors of nitric oxide, including alkyl nitrites, thionitrites and C-nitroso compounds, can be added through an analogous set of manipulations; such chemistry is well-known in the literature.

A preferred inhibitor is the nitrated xanthine oxidase inhibitor nitrated allopurinol derivative which is 1,5-bis(3-nitrooxypropyl)-1,5-dihydro-4H-pyrazolo[3,4-d]pyrimidin-4-one and has the formula:

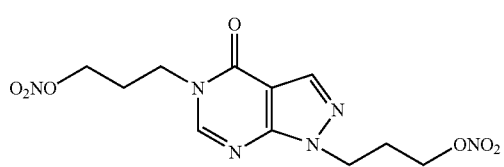

(16)

Nitrated allopurinol (16) can be prepared, for example, as described in Working Example I herein.

We turn now to the second embodiment of the invention herein, which is directed a method of treating a patient with a disorder associated with oxidative stress, comprising administering to that patient a therapeutically effective amount of an inhibitor of the first embodiment herein.

The term "associated with oxidative stress" as used in the above paragraph means a hazardous level of reactive oxygen species.

The disorders associated with oxidative stress for the second embodiment herein include heart failure, stable angina, ischemic reperfusion injury, sickle cell disease, diabetes involving leg pain, Parkinson's Disease, ALS, AIDS dementia, stroke, neuropathic pain, Alzheimer's disease, lung injury, cystic fibrosis and asthma.

As indicated above, the treating agents for the second embodiment are the inhibitors of the first embodiment.

The therapeutically effective amount for the second embodiment is an amount which mediates amelioration of symptoms of the disorder treated. Where the disorder is heart failure, the therapeutically effective amount is an amount which mediates amelioration of acute coronary symptoms and/or myocardial infarction. Where the disorder is stable angina, the therapeutically effective amount is an amount which mediates reduction or elimination of pain. Where the disorder is ischemic reperfusion injury, the therapeutically effective amount is an amount effective to mediate symptoms of pain, organ damage and/or arrhythmia (symptoms can be variable). Where the disorder is diabetes involving leg pain, the therapeutically effective amount is an amount effective to mediate a decrease in leg pain and walking distance increase. Where the disorder is sickle cell disease, the therapeutically effective amount is an amount which mediates red cell vasodilation and amelioration of pain, organ damage, lack of blood flow or pathological clotting. Where the disorder is atherosclerosis, the therapeutically effective amount is an amount which ameliorates symptoms of hyperlipidemia. Where the disorder is Parkinson's disease, the therapeutically effective amount is an amount that stabilizes motor or tremor function. Where the disorder is ALS, the therapeutic amount is an amount that slows deterioration. Where the disorder is stroke, the therapeutically effective amount is an amount that decreases infarct size or improves symptoms. Where the disorder is Alzheimer's disease, the therapeutically effective amount is an amount that slows memory loss.

In general, the amount administered daily ranges from 1 to 1,000 mg with selection within the range being determined by the drug administered, the disorder being treated and the severity of symptoms. For nitrated allopurinol (16), amount administered on a daily basis ranges, for example, from 100 to 800 mg with from 200 to 700 mg/day being preferred for treatment of heart failure and from 200 to 700 mg/day being preferred for treatment of stable angina and 300 mg/day being an average dose.

Suitable routes of administration for the second embodiment include, for example, oral administration.

We turn now to the third embodiment of the invention herein, which is directed at a method of treating an ischemic disorder in a patient having such disorder, comprising administering to that patient an amount of inhibitor of the first embodiment effective to mediate conservation of oxygen and vasodilation.

The disorders treated in the third embodiment include, for example, sickle cell disease, heart failure, angina and lung inflammation.

Mediation of conservation of oxygen is manifested by improved symptoms, change in NADH to NADPH ratio, change in tissue oxygen concentration, change in tissue pH or change in oxygen to ATP utilization ratio.

Mediation of vasodilation is manifested by change in blood flow, blood pressure or symptoms.

As indicated above, the treating agents are those of the first embodiment herein; nitrated allopurinol (16) is a preferred treating agent.

Effective amounts of treating agents for the third embodiment generally range from 1 to 1,000 mg on a daily basis with the amounts for nitrated allopurinol (16) generally ranging from 100 to 800 mg on a daily basis, preferably from 200 to 700 mg on a daily basis, with selected amounts within the general range depending on the treating agent used, the disorder treated and the severity of the symptoms.

Routes of administration for the third embodiment include, for example, oral.

We turn now to the fourth embodiment herein, which is directed to a method of providing contraction of heart, skeletal or smooth muscle matched to appropriate oxygen utilization in a patient in need thereof, comprising administering to that patient a therapeutically effective amount of inhibitor of the first embodiment.

The patients in need of contraction of heart muscle matched to appropriate oxygen utilization include those, for example, with heart failure. The patients in need of contraction of skeletal muscle matched to appropriate oxygen utilization, include, for example, patients with skeletal muscle weakness or respiratory failure. The patients in need of contraction of smooth muscle matched to appropriate oxygen utilization are those, for example, with angina.

As indicated above, the treating agents for the fourth embodiment herein are those of the first embodiment; nitrated allopurinol (16) is the preferred treating agent for the fourth embodiment.

Therapeutically effective amount of treating agent for the fourth embodiment is an amount which ameliorates pathological increase in energy or oxygen consumption or pathological increase in radical formation. The pathological increase in energy consumption is determined by determining amounts or ratios of oxygen to ADP or phosphocreatine or NADH to NADPH, the pathological increase in oxygen consumption being determined by determination of increase in reactive oxygen products or increase or decrease in venous oxygen gradient or organ dysfunction and the pathological increase in radical formation being determined by increased reactive oxygen production as measured using various standard approaches.

In general, therapeutic amounts for the treating agents for the fourth embodiment range from 1 to 1,000 mg on a daily basis and therapeutic amount for nitrated allopurinol (16) generally ranges from 100 to 800 mg on a daily basis preferably ranging from 200 to 700 mg on a daily basis, with particular amounts within the general range selected varying with treating agent, disorder treated and severity of symptoms. Routes of administration for the fourth embodiment include, for example, oral.

The invention herein is supported by and illustrated by the following background and working examples.

WORKING EXAMPLE I

Synthesis of Nitrated Allopurinol (16)

1,5-Bis(3-chloropropyl)-1,5-dihydro-4H-pyrazolo[3,4-d]pyrimidin-4-one (14)

To a stirred mixture of 6 (allopurinol, lactam form) (4.08 g, 30 mmol) in anhydrous DMF (60 mL) was added cesium carbonate (11.73 g, 36 mmol) at 0° C. in one portion. 1-Chloro-3-iodopropane 13 (3.22 mL, 30 mmol) was then added within 1 min, and the whole mixture was stirred at 0° C. for 10 h, and then warmed to the ambient temperature with stirring for additional 12 h. The resulting white suspension was poured into ice-cold $H_2O$ (200 mL), extracted with EtOAc (500 mL), washed with brine (3×60 mL) and dried. The crude products were purified by flash chromatography (eluting with 40-75% EtOAc in hexane) to give 14 (2.35 g, 27% yield) as a white solid. $^1$H NMR (300 MHz, $CDCl_3$): δ 2.26 (m, 2H), 2.36 (m, 2H), 3.52 (t, 2H, J=6.0 Hz), 3.55 (t, 2H, J=6.6 Hz), 4.15 (t, 2H, J=6.9 Hz), 4.48 (t, 2H, J=6.9 Hz), 7.99 (s, 1H), 8.05 (s, 1H); $^{13}$C NMR (75 MHz, $CDCl_3$): δ 31.61, 32.60, 41.79, 41.94, 44.35, 44.82, 106.02, 135.36, 149.21, 151.75, 157.23.

1,5-Bis(3-nitrooxypropyl)-1,5-dihydro-4H-pyrazolo[3,4-d]pyrimidin-4-one (16)

Sodium iodide (1.8 g, 12 mmol) was added to a solution of 14 (0.90 g, 3.1 mmol) in anhydrous acetone (30 mL), and the solution was then heated at reflux for 8 h, resulting in a light-green suspension. After cooled to rt, the suspension was filtered off, and the filtrate was condensed to dryness. The solid residue was suspended in $CH_2Cl_2$ (60 mL), filtered off again, and the filtrate was condensed to dryness, pumped for 30 min, giving crude di-iodide 15 (1.36 g) as a white solid.

To a stirred solution of the crude di-iodide 15 (1.2 g) in anhydrous $CH_3CN$ (20 mL) was added silver nitrate (1.53 g, 9 mmol), and stirred at rt for 15 h, resulting in a yellow suspension. The suspension was filtered off, rinsing with EtOAc, and the filtrate was diluted with EtOAc (300 mL), washed with $H_2O$ (2×50 mL), and dried. The crude products were purified by flash chromatography (eluting with 50% EtOAc in hexane), affording an unidentified compound (0.27 g, white solid), followed by di-nitrate 16 (0.17 g, 20% yield) as a white solid. The NMR spectral data for 16 are given as follow: $^1$H NMR (400 MHz, $CDCl_3$): δ 2.19 (m, 2H), 2.27 (m, 2H), 4.06 (t, 2H, J=7.2 Hz), 4.40 (t, 2H, J=6.0 Hz), 4.38 (t, 2H, J=6.6 Hz), 4.47 (t, 2H, J=6.0 Hz), 7.89 (s, 1H), 8.01 (s, 1H); $^{13}$C NMR (100 MHz, $CDCl_3$): δ 26.99, 27.08, 43.65, 43.82, 70.02, 70.19, 105.93, 135.60, 149.06, 151.84, 157.19; FAB-MS: m/z 343 ([M+1]$^+$, 85).

BACKGROUND EXAMPLE I

Figure 1B:
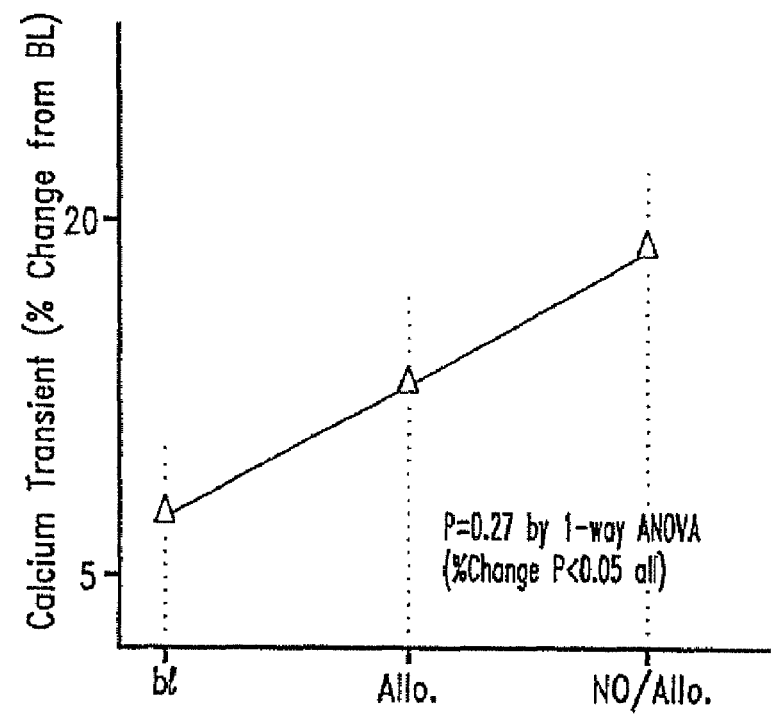
FIG. 1(b) is a graph of Systolic Calcium Transient (% change from baseline) for baseline, allopurinol administration and nitrated allopurinol administration and depicts results of Background Example 1.

Isolated cardiac myocytes from nNOS deficient rats (known to have increased xanthine oxidase activity), were evaluated for responses at baseline (BL or bl), then to allopurinol, then to nitrated allopurinol. The concentration of allopurinol used was 0.5×10$^{-3}$ M. The concentration of nitrated allopurinol used was 10$^{-4}$M. Evaluation was carried out for sarcomere length (SL), a measure of myocardial contraction, and for systolic calcium transient which drives myocardial contraction. The results for evaluation of sarcomere length are shown in FIG. 1A and results for evaluation of systolic calcium transient are shown in FIG. 1B. As shown in FIGS. 1A and 1B, these parameters are shown to rise in parallel, with increase obtained for nitrated allopurinol being greater than increase obtained for allopurinol (not nitrated). The data shows the drugs augment myocardial contractibility, at the level of excitation—contraction coupling.

WORKING EXAMPLE II

A 27-year old black female presents with a dilated cardiomyopathy and is begun on a standard regimen including ace inhibitors, diuretics, and digoxin with little improvement. She is begun on nitrated allopurinol (16), 300 mg PO BID, with improvement of left ventricular function and a decrease in a shortness of breath over the ensuing week.

WORKING EXAMPLE III

A 70-year old white female with class 3 angina is begun on nitrated allopurinol (16), 300 mg/day. Her classification improved to class 2 over two weeks.

WORKING EXAMPLE IV

A 55-year old white male has a crush wound to his left lower extremity and undergoes emergency surgery. Because the wound has been ischemic for six hours, the patient was begun on nitrated allopurinol (16) and shows no aggravation of injury following revascularization.

WORKING EXAMPLE V

A 30-year old black male with sickle cell disease presents with pulmonary hypertension and LFT abnormalities. He had had four admissions to the emergency in the past year with painful crisis. He is begun n 300 mg/day of nitrated allopurinol (16) with a decrease in his pulmonary artery pressure over the following year from a mean of 35 mm Hg to 30 mm Hg. His LFT abnormalities resolve and he has only one painful crisis.

WORKING EXAMPLE VI

A 45-year old white male with hyperlipidemia and a family history of premature coronary disease shows extensive calcification of his coronaries and aorta by MRI and coronary exam. He is begun on nitrated allopurinol (16), 300 mg/day, with mild regression of his disease over the following two years.

WORKING EXAMPLE VII

A 48-year old white male with bleomycin-induced lung injury is begun on nitrated allopurinol (16), 300 PO BID. The $PO_2$ improves from 60 (on 100% oxygen) to 65 mm Hg on 50% oxygen over the following week.

WORKING EXAMPLE VIII

Working Example III provides an example of conservation of oxygen combined with vasodilation. Working Example V provides an example of vasodilation.

WORKING EXAMPLE IX

A 60-year old with congestive heart failure and a dilated cardiomyopathy is begun on nitrated allopurinol (16), 300 mg POQD. One week later, his ejection fraction had improved from 35% to 40%, his blood pressure had decreased from 130/80 to 110/80, and his $pO_2$ has improved from 70 to 80 mm Hg on room air. Symptoms on angina had also decreased.

WORKING EXAMPLE X

A 70-year old with Parkinson's disease treated with L-dopa has persistent tremor and motor problems. After three weeks of nitrated allopurinol (16), 300 mg/day, symptoms improve.

WORKING EXAMPLE XI

A 65-year old with Alzheimer's disease is begun on 300 mg/day nitrated allopurinol (16). His memory and cognitive function stabilizes after 3 months.

WORKING EXAMPLE XII

A 75-year old with leg pain and diabetes, who is unresponsive to treatment, is begun on nitrated allopurinol (16), 300 mg/day, and the distance he can walk improves and pain decreases.

WORKING EXAMPLE XIII

A 35-year old with ALS with progressive deterioration, stabilizes after three weeks at 300 mg/day of nitrated allopurinol (16).

WORKING EXAMPLE XIV

A 40-year old asthmatic with frequent exacerbations is begun on 300 mg/day nitrated allopurinol (16). Steroid use is successfully tapered.

Variations

Variations will be obvious to those skilled in the art. Therefore, the scope of the invention is defined by the claims.

What is claimed is:

1. A method for treating leg pain in a patient with leg pain associated with diabetes comprising administering to the patient bis(3-nitrooxypropyl)-1,5-dihydro-4H-pyrazolo[3,4-d]pyrimidin-4-one in an amount to mediate a decrease in leg pain or an increase in walking distance compared to the walking distance before treatment.

* * * * *